United States Patent [19]

Lowman

[11] Patent Number: 5,234,421
[45] Date of Patent: Aug. 10, 1993

[54] DIAPER FOR INCONTINENT DOGS

[76] Inventor: Joy Lowman, 16730 Tranquil Dr., Sugar Land, Tex. 77478

[21] Appl. No.: 616,229

[22] Filed: Nov. 20, 1990

Related U.S. Application Data

[63] Continuation-in-part of Ser. No. 493,759, Mar. 15, 1990, abandoned.

[51] Int. Cl.⁵ .............................................. A61F 13/15
[52] U.S. Cl. ................................. 604/385.1; 604/389; 119/95
[58] Field of Search ............... 119/95, 143; 604/385.1, 604/385.2, 386, 387, 389, 390, 393, 394, 397, 401, 402

[56] References Cited

U.S. PATENT DOCUMENTS

| | | | |
|---|---|---|---|
| 2,539,606 | 1/1951 | Bailey | 119/143 |
| 3,211,132 | 10/1965 | Hersh | 119/143 |
| 3,656,459 | 4/1972 | Missud | 119/95 |
| 4,510,887 | 4/1985 | Lincoln et al. | 119/95 |
| 4,527,991 | 7/1985 | Msarsa | 604/399 |
| 4,577,591 | 3/1986 | Wesseldine | 604/398 |
| 4,779,573 | 10/1988 | Vidal | 119/95 |
| 4,917,683 | 4/1990 | Thompson | 119/95 |

FOREIGN PATENT DOCUMENTS 943116  11/1963  United Kingdom ................ 119/143

Primary Examiner—Randy C. Shay
Assistant Examiner—K. Reichle
Attorney, Agent, or Firm—Gunn, Lee & Miller

[57] ABSTRACT

A canine diaper is set forth and is comprised of three sheets of material. The outer sheet is a thin flexible waterproof sheet, the next sheet is an absorbent pad of multi-plyed construction, and the inner sheet is porous, and the diaper is shaped with a central tail hole in a strip which extends from the tail above and below the body terminating in four tabs which reach adjacent the ribs for fastening by adhesive strips.

6 Claims, 1 Drawing Sheet

DIAPER FOR INCONTINENT DOGS

This application is a continuation-in-part of application Ser. No. 493,759 which was filed on Mar. 15, 1990 and which has now been abandoned.

BACKGROUND OF THE DISCLOSURE

The present disclosure is directed to a diaper for incontinent dogs, both male and female. Moreover, it is adapted for use with older dogs which have become messy because of age. Alternately, it can be used with younger dogs which are momentarily afflicted with various ailments, all for a short interval until the dog reestablishes control and does not mess or soil the immediate vicinity.

As long as people live in congregated areas, and as long as they keep pets, it is axiomatic that people will keep dogs in the house, mostly indoors for city dwellers. In contrast with an outdoor dog, such as one that stays at the barn or in the pasture, a house bound dog runs the risk of messing the interior area, and this is particularly true of older or sick dogs.

Newborn puppies typically are house broken after just a few weeks and a pleasant state of affairs is established with the owner. As the dog becomes older and the family attachment becomes stronger, sometimes the dog loses its control much to the upset and chagrin of the family, especially where the dog normally stays indoors. This is particularly a problem with older dogs, but it is also a momentary problem with dogs that are being medically treated, perhaps recovering from an ailment, injury or the like. Suffice it to say, incontinence and loss of control in general whether occasioned by old age, injury or ailment creates a problem for a house kept dog and the dog owner.

The present disclosure sets forth a kind of diaper which is intended for use with the dog. In particular, it is constructed in the form of an elongate pad having corner located tabs. There are four tabs, and they extend parallel to one another from opposite edges of the pad. The four tabs thereby enable the user to install the diaper on the house pet with a view of reducing consequences, that is, reducing the mess occasioned by loss of control of the older or sick dog. In this instance, it is particular helpful so that the difficulties resulting therefrom, whether permanent or temporary, can be reduced, and hopefully eliminated.

The present disclosure is a disposable diaper readily affixable to a dog. It is constructed in the form of an elongate pad. One particular feature is an opening or hole cut into the pad. The tail hole is sealed by a waterproof strip containing openings through which the tail is positioned. A strip of this nature provides a better seal around the dog's tail than would a mere hole or other opening, enhancing the ability of the diaper to prevent leakage caused by activity or movement of the animal.

Additionally, use of the strip provides better protection on a greater variety of dogs. For a particular size of the present apparatus, a device which can be scaled for larger or smaller dogs, there is some variety in tail dimensions including the diameter of the base of the tail, and the relative position of the tail on the dog, i.e. whether the tail is relatively high or low on the hind quarters. Additionally, the angle of deflection is different for each animal, meaning some dog's tails are carried high (e.g., a Beagle) while others point downward. In either case, the present apparatus is installed by sliding the tail through an opening provided in the strip, registering the diaper on the dog. Due to the various placement of the tail on the animal, the use of such a diaper provides greater latitude in the positioning of the diaper around the animal while still maintaining an effective seal.

The pad is wrapped in a U-shaped fashion around the body of the dog, partly over the top and partly below the hind quarters, thereby aligning the four tabs, two of the tabs on top and two on the bottom in corresponding positions on the left and the right of the animal. The tabs are easily attached to their opposing tabs by adhesive strips, thereby fixing the diaper to the dog. Removal is easily accomplished by simply peeling off the adhesive strips joining the tabs, thereby permitting diaper removal.

The present apparatus is a throw-away diaper which can then be discarded. It is constructed with multiple plies of material which may be biodegradable. The outer or exposed ply is a waterproof strength ply. The intermediate ply is an absorbent ply which preferably extends close to and parallel to the edges but it need not extend completely to the edges of the outer ply. The third ply is equal in area and similar in shape to the outer waterproof ply and it has edges that correspond the the outer ply. The third or inside ply is particularly provided for strength to hold the diaper together even when wet, but is sufficiently porous to enable the absorbent middle ply to accomplish its intended purpose.

While the foregoing summarizes the structure of the present disclosure, details of its construction and its mode of use or installation are set forth below with the description of the preferred embodiment.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
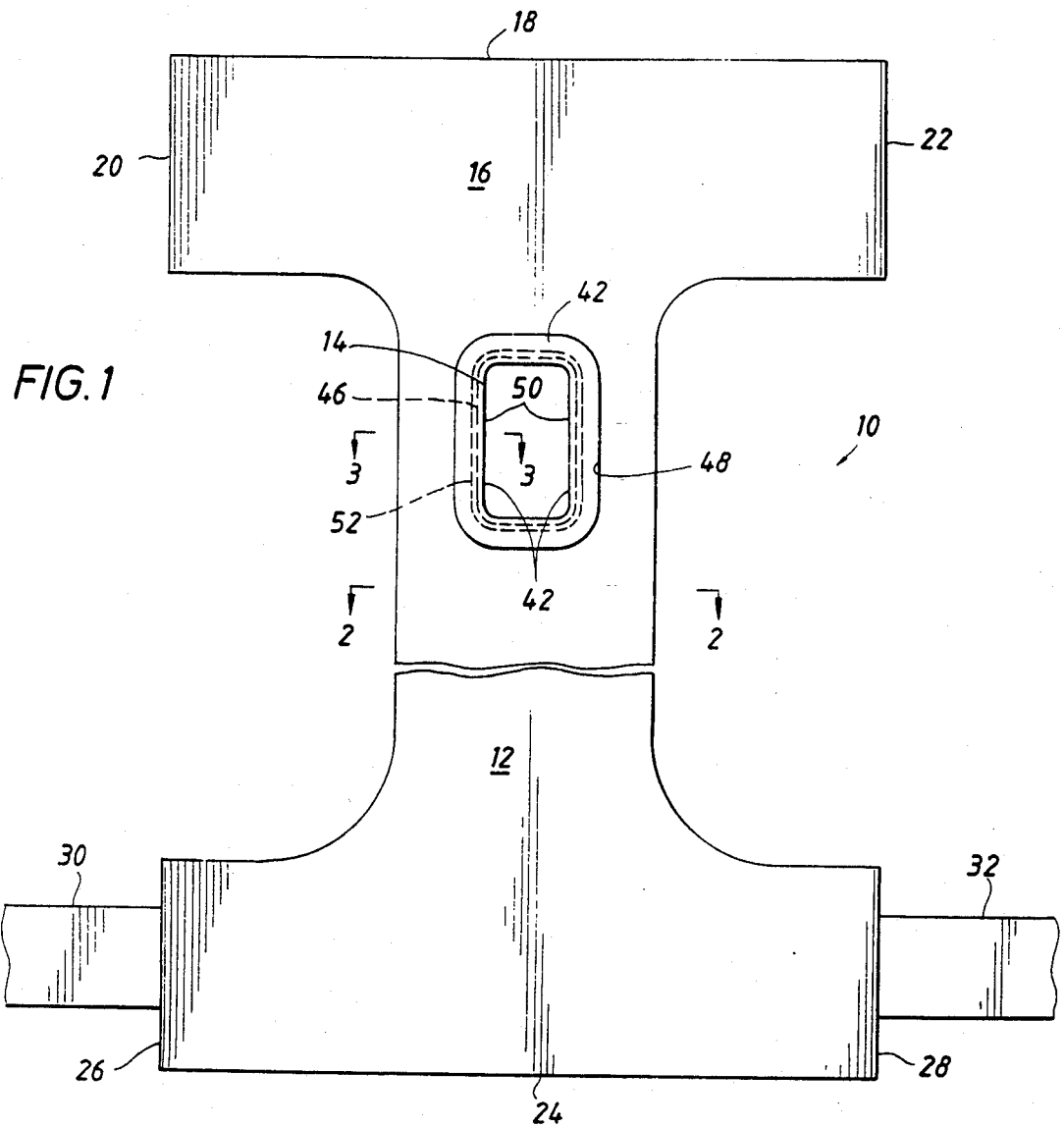
FIG. 1 shows a diaper in accordance with the teachings of the present disclosure which is constructed with an elongate pad which extends outwardly into four tabs at the corners thereof, and the four tabs aligned so that the diaper can be affixed to a dog. The diaper further includes an opening for the tail which is defined between two opposing adhesive planar sheets, with the strips containing slits the protrusion of the animal's tail.

Attention is now directed to FIG. 1 of the drawings where the diaper 10 of the present disclosure is shown. This view shows the shape of the diaper and includes features important to its successful use. As will be understood, the diaper 10 can be scaled to different sizes for large or small dogs. It is believed that the description given hereinafter will suffice for a representative size, and it can be scaled from that size to other sizes. The diaper 10 will be described as a planar member, it being understood that the diaper is folded and placed on the dog in the fashion set forth below. In addition, a description will be given of the constituent layers of the diaper. The diaper 10 has a pad region 12. The pad region is located below a tail hole 14. The tail hole is spaced from another region 16 which will be described as the back strap. This is a strap that fits in the fashion of an inverted U on the back of the dog and which is located forward of the tail and which extends against left and right ribs of the dog forward of the hind quarters. The back strap 16 is sufficiently long at the dimension 18 that it extends approximately fifty to seventy percent around the girth of the dog. The location is preferably about even with the kidneys or over the ribs of the dog. It need not stretch up to the chest region. The dimension 18 terminates at the left tab 20 and there is a symmetrical or right tab 22. As shown in the drawings, the entire structure is symmetrical along a centerline vertically through FIG. 1.

The tabs 20 and 22 are of equal width. The tail opening 14 is offset from the tabs 20 and 22 by a distance which accommodates the position of the tail on the body of the dog. Surprisingly, there is a good deal of variety between dogs of comparable weight or size. The variety arises in part with breeds, and this is manifest by the positioning of the tail on the body, relatively speaking. Moreover, the angle and size of the tail may vary. For that reason, a relatively long rectangle 14 is cut so that it will coincide with the region of the tail. To prevent leakage through the tail hole 14 and to provide a wider range of diaper placement, the tail hole 14 is marginally sealed with two adhesive strips which border the tail hole through which the tail is placed. This permits the tail to protrude through the tail hole 14 with some clearance while still maintaining an effective seal. It is also useful as a type of alignment or locator mark on the diaper. In other words, when the tab 20 and 22 and central portion 16 are positioned on the dog forward of the tail, diaper location is somewhat limited by the position of the diaper referenced to the tail of the dog.

The dimension 24 of the diaper 10 is preferably equal in length to the dimension 18. It terminates at left and right tabs 26 and 28. These tabs also are approximately equal in length to the tabs 20 and 22. The tabs 26 and 28 are positioned opposite the tabs 20 and 22 respectively. Thus, the tab 20 will be located on the left side of the dog extending from above the dog while the tab 26 is positioned on the left side of the dog extending upwardly from below. The dimension 24 is folded into a U-shape which positions the tabs 26 and 28 so they can reach up the sides of the dog approximately even with the tabs 20 and 22. This locates the tabs 26 and 28 approximately even with the kidneys or even with the rib cage. All four tabs are located forward of the hind quarters. The tabs 26 and 28 fold up and over the ends of the tabs 20 and 22. The dimensions 18 and 24, preferably equal, provide sufficient surplus length that the two tabs overlapping on the left and the two overlapping on the right can be fastened together. As a generalization, the dimensions 18 and 24 are preferably equal, and the sum of these two dimensions is greater than the circumference of the dog. This permits some overlap at the tabs.

The tabs are positioned one over the other, i.e., the tab 26 overlays the tab 20, or in reverse fashion. The tabs are thus joined when they overlap. To this end, short adhesive tabs 30 and 32 of suitable length are also included, and they adhere on the exposed exterior waterproof surface of the diaper 10. These tabs are preferably supplied with the adhesive on the adhesive tapes 30 and 32 folded so that the adhesive side adheres at a location out of the way and so that the tabs 30 and 32 can be extended to lap over the opposing tabs 20 and 22 thereby anchoring the diaper on the dog. The tab 30 is extended from the stored and folded position, and then it is lapped over the tab 20 and adheres to that tab. The same is accomplished on the other side.

Figure 2:
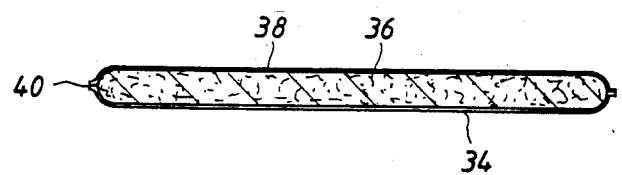
FIG. 2 is a sectional view through the diaper of FIG. 1 along the line 2—2 and showing the layered construction of the three plies of material.

Going to FIG. 2 of the drawings, it will be observed that the diaper 10 is formed of three plies of material. First of all, there is an outer ply 34 which is a waterproof thin layer. It is typically in the range of about one to four mils thick and is preferably a thin sheet plastic which is waterproof. It is fairly strong and resists tearing. In addition to that, there is another surface layer on the opposite side. These two layers hold therebetween an absorbent layer 36. The layer 36 is formed of multiple plies of absorbent material. It is woven or felted in the fashion of mesh or the like. Moreover, the absorbent pad forms a fairly thick sandwich between the outer layers, the layer 36 having an uncompressed thickness of up to about one centimeter. The absorbent layer need not have the width of the exposed surface layer 34. Therefore, the layer 36 is only slightly smaller in dimensions. The exposed surface ply 38 is opposite the outer surface ply 34. The layer 38 is relatively thin and yet it is porous. It is porous so that moisture can be absorbed into the absorbent ply therebetween. The ply 38 is therefore highly porous and able to admit moisture. It is, however, still somewhat strong. It is about the same in thickness as the layer 34. The layer 38 is preferably formed of an elastomeric material which is similar to the elastomeric material used in the surface layer 34.

The layers 34 and 38 join at the common edges around the periphery and at the hole 14. There, one method of joinder is machine stitching or, preferably, they are heat bonded into a common beaded seam. This defines the seam so that it is complete, there being a seam all the way around the opening 14.

In order to maintain a superior seal around the tail of the dog while maintaining a greater range of possible tail position and animal size, the tail hole 14 is sealed within two adhesive strips 42 and 44. The exterior strip 42 is a thin waterproof adhesive strip positioned as shown, completely covering the tail hole 14 and maintaining sufficient contact with the outer sheet 34 to provide adequate adherence. The interior adhesive strip 44 is a thin porous adhesive strip positioned as on the opposite face, completely covering the tail hole 14 and maintaining sufficient contact with the inner sheet 38 to provide adequate adherence. The two strips contact each other in the hole and are cut away to leave marginal edges or beads around the hole where the two strips seal adhesively.

DESCRIPTION OF THE PREFERRED MATERIALS

The layer 36 is absorbent layer which is intended to hold moisture. It is a biodegradable product of Weyerhaeuser which is approximately 88% biodegradable and is primarily formed of wood fluff pulp and related tissue which is primarily cellulose and also may include a cornstarch filled cover. The layers 34 and 38 are sheet material, typically of about one mill thickness. An important feature of the present construction is the mode in which the tail opening is formed. Briefly, the layers 34, 36, and 38 are cut with a rectangular opening of a certain size. Using a conventional die cutter, a rectangular hole is cut. More importantly, the thin sheet film members 34 and 38 are cut to a certain dimension, but, because of the felting of the innermost layer 36, it tends to cut and tear away so that the opening punched through the layer 36 is slightly larger than the opening in the layers 34 and 38. After that, the large opening is patched by adhering an outside film strip to the layer 34 and an external film strip to the layer 38. The inside layer 38 is closed by sealing it with a strip of surgical tape bearing the trademark "Micropore", which is a product of the Three M firm. It is a porous tape which permits the free passage of air and moisture through the tape. The tape is porous to air and moisture vapor transmission. In the descriptive literature regarding this product, the tape is formed with a synthetic polymeric acrylate adhesive which has a backing typically formed of rayon fibers yielding a product which is approximately 0.005 inches thick. This is shown at 42 in FIG. 1 of the drawings.

Figure 3:
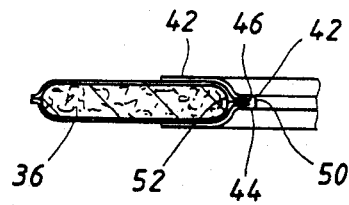
FIG. 3 is a detailed sectional view along the line 3—3 of FIG. 1 showing the seams joining the outer and inner layers at a border.

On the exterior face of the diaper, a similar, preferably equal strip is affixed to cover over the opening previously formed in the layers 34, 26, and 38. This is a layer of tape from the same Three M firm and bears the model number 2185 matte white film tape. The tape has a white matte finish on a polypropylene film with an adhesive. A rubber tacky adhesive is preferred. The thickness is approximately about 4 mils. The two strips of material are coextensive in area. They cover over and marginally adhere to the respective layers around the rectangular hole. In FIG. 1 of the drawings, this marginal region of adherence is illustrated. Thus, the rectangular openings in the layers 34 and 38 are identified by the hidden lines 46, while the adhesive margin 48 identifies the area where the layers 42 and 44 adhere to the areas which they contact. The two strips of film thus join as shown at one edge of the tail hole as shown in FIG. 3. That is, FIG. 3 shows how the strips 42 and 44 join to the body of the diaper surrounding the cut opening and extend into that opening and adhere to each other on the interior of the strip borders at 48. This forms a sealed seam. Preferably, the two strips 42 and 44 are stamped with a cutting die which forms an opening in the two of them, this die being somewhat smaller than the hidden cut line at 46 which is made by a larger die. This inner edge is identified at 50. The difference in dimensions is relatively small but is sufficient to permit marginal contact of the two strips 42 and 44 to thereby complete a closure or seam around the tail opening 14. The tail hole has a width B equal to about 40 to 60% of the strips 42 and 44.

As can be seen, fabrication is quite easy and straight forward. The first step is to cut through the layers 34, 36, and 38 by means of rectangular die cutting apparatus. Precautions are made to cut the absorbent layer 36 at the line 52 so that it is cut to form a hole having a larger dimension and the edge is back and out of the way. The next step is to adhere the two rectangular adhesive patches 42 and 44 so that they are closely aligned with each other and the two join to close over and seal the opening. Then, the third step is carried out, namely cutting a smaller rectangular opening through the two strips, leaving an encircling margin so that they join. This forms a seam at 50 closing the marginal edge or gap into the absorbent layer 36. This seam is leak proof. This seam is closed by this mode of manufacture. It provides a highly reinforced tail opening which will not tear at the relative narrow width of the diaper as shown in FIG. 1. The completed product can be successful sized to several sizes and fitted on a dog in the manner of operation as described below.

In operation, the device of the present disclosure is installed on an appropriately sized dog. The diaper can be made to size for the smallest and the largest dogs. For a particular sized dog, and one on which the dimensions are properly selected, the device is placed on the dog in the following fashion. The dog's tail is threaded through the opening and centered in the tail hole 14. The tabs 20 and 22 are pulled over the back of the dog so that the diaper 10 extends along the back of the dog for some distance and the tabs 20 and 22 are folded downward. They are deployed on opposite sides of the dog adjacent either the kidneys or the ribs. At the same instant, the reminder of the diaper is installed by folding the entire diaper downward, and then extending it forwardly of the dog so that the tabs 26 and 28 can be folded upwardly in front of the hind quarters of the dog. The tabs 26 and 28 align with tabs 20 and 22. The four tabs are positioned, two on the right and two on the left. When so positioned, the adhesive tabs 30 and 32 are unfolded and extended so that they adhere to the tabs 20 and 22 above. The tabs thus position the absorbent pad 36 within the diaper so that it is practically impossible for the dogs to form an untidy mess. The diaper is strategically placed on the dog so that soiling of the domestic area is prevented. Accordingly, this apparatus is particularly helpful in cleanliness where the dog has the run of the place.

While the foregoing is directed to the preferred embodiment, the scope thereof is determined by the claims which follow.

What is claimed is:

1. A diaper for a dog comprising:
    (a) an elongate multi-layered strip wherein said strip has upper portion means for extending forwardly of a tail of the dog and along and above the back of the dog to the rib area of the dog when installed on the dog, said upper portion means having side edges and tabs extending laterally at said side edges, respectively, said strip further comprising lower portion means for extending forward of the tail of the dog and along and below the body of the dog to the rib area of the dog when installed on the dog, said lower portion means having side edges and tab means extending laterally at said side edges, respectively, for releasable affixing to said corresponding tabs on said upper portion means to fasten the diaper on the dog, the multi-layered strip further comprising three flexible planar sheets comprising an outer sheet formed of a waterproof strength layer, a middle sheet formed of absorbent means for absorbing body waste fluids and an inner sheet formed of a fluid permeable layer, said planar sheets being positioned in a superposed relationship; and
    (b) a hole through said planar sheets between said upper and lower portion means defining means for receiving the tail of the dog therethrough when the diaper is installed on the dog, said hole having a continuous periphery, the edges of said planar sheets defining said hole being joined together and said periphery including means for sealing said tail hole against leakage.

2. The apparatus of claim 1 where the hole through said middle sheet has a greater size than the hole through said outer and inner sheets, the edges of said outer and inner sheets defining said hole and being directly joined together without joining of the middle sheet to thereby seal said middle sheet between the outer and inner sheets.

3. The apparatus of claim 2 wherein said sealing means includes an outer adhesive strip adhesively joined to the outer sheet around the periphery of the hole therein and an inner adhesive strip adhesive joined to the inner sheet around the periphery of the hole therein, said strips including a hole therethrough of smaller size than the hole through said outer and inner sheets and aligned therewith to define means for receiving the tail of the dog therethrough when the diaper is installed on the dog, said hole through said strips having a continuous periphery, the edges of said strips defining said hole being joined together within the open area of the hole defined by said outer and inner sheets, said outer adhesive strip comprising a waterproof adhesive strip and said inner adhesive strip comprising a fluid permeable adhesive strip.

4. The apparatus of claim 3 where said tab means include means for releasably adhesively affixing said tab means to said corresponding tabs or said upper portion.

5. The apparatus of claim 3, wherein the hole through said planar sheets has a width equal to about forty to sixty percent of the width of said outer and inner adhesive strips.

6. The apparatus of claim 3, wherein at least one of said flexible sheets is formed of biodegradable materials.

* * * * *